United States Patent
Moody et al.

(10) Patent No.: US 11,872,037 B2
(45) Date of Patent: Jan. 16, 2024

(54) SINGLE PART BANDAGE AND METHOD FOR A MEDICAL SENSOR

(71) Applicant: Covidien LP, Mansfield, MA (US)

(72) Inventors: Derek L. Moody, Longmont, CO (US); Shai Fleischer, Modiin (IL); Jacob Dove, Lafayette, CO (US); Sarah L. Hayman, Boulder, CO (US); Linden A. Reustle, Milliken, CO (US)

(73) Assignee: COVIDIEN LP, Mansfield, MA (US)

( * ) Notice: Subject to any disclaimer, the term of this patent is extended or adjusted under 35 U.S.C. 154(b) by 424 days.

(21) Appl. No.: 16/904,660

(22) Filed: Jun. 18, 2020

(65) Prior Publication Data

US 2021/0393171 A1 Dec. 23, 2021

(51) Int. Cl.
*A61B 5/1455* (2006.01)
*A61B 5/00* (2006.01)

(52) U.S. Cl.
CPC ........ *A61B 5/1455* (2013.01); *A61B 5/68335* (2017.08); *A61B 2562/12* (2013.01); *A61B 2562/146* (2013.01); *A61B 2562/182* (2013.01)

(58) Field of Classification Search
CPC .......................... A61B 5/1455; A61B 5/14552
See application file for complete search history.

(56) References Cited

U.S. PATENT DOCUMENTS

| | | |
|---|---|---|
| 6,748,254 B2 | 6/2004 | O'Neil et al. |
| 7,113,815 B2 | 9/2006 | O'Neil et al. |
| 7,650,177 B2 * | 1/2010 | Hoarau ................ A61B 5/6838 600/323 |
| 8,433,383 B2 | 4/2013 | O'Neil et al. |
| 8,452,366 B2 | 5/2013 | Gilland |
| 8,692,992 B2 | 4/2014 | Besko |
| 8,726,496 B2 | 5/2014 | Besko |
| 9,161,722 B2 | 10/2015 | Besko et al. |
| 9,265,464 B2 | 2/2016 | O'Neil et al. |
| 9,351,685 B2 | 5/2016 | O'Neil et al. |
| 9,610,040 B2 | 4/2017 | Besko |
| 10,098,577 B2 | 10/2018 | Besko et al. |
| D862,709 S | 10/2019 | Besko et al. |

(Continued)

FOREIGN PATENT DOCUMENTS

| | | |
|---|---|---|
| WO | 2008133170 A1 | 11/2008 |
| WO | 2019222615 A1 | 11/2019 |

OTHER PUBLICATIONS

International Application No. PCT/US2021/037726 International Search Report and Written Opinion dated Oct. 4, 2021, 14 pages (MD40374PCT).

*Primary Examiner* — Marjan Fardanesh
(74) *Attorney, Agent, or Firm* — Fletcher Yoder, P.C.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor includes a bandage that is constructed as a single piece such that plural layers of the bandage are configured together to allow for a leaflet opening of the bandage, for example using at least one removable liner or tab, to insert a pulse oximetry circuit therein.

20 Claims, 6 Drawing Sheets

(56) References Cited

U.S. PATENT DOCUMENTS

| | | |
|---|---|---|
| 2002/0045807 A1 | 4/2002 | Al-Ali et al. |
| 2014/0228659 A1 | 8/2014 | Besko |
| 2019/0167161 A1 | 6/2019 | Al-Ali et al. |
| 2020/0113496 A1 | 4/2020 | Scruggs et al. |

* cited by examiner

SINGLE PART BANDAGE AND METHOD FOR A MEDICAL SENSOR

FIELD

The present disclosure relates generally to medical devices, and more particularly, to medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

One issue in such sensors relates to manufacturing of such sensors, including with regard to ease of manufacture, reliability of the manufactured sensor, repeatability of manufacture for large numbers of manufactured sensors, as well as ease, reliability, repeatability, etc. for the re-manufacture of sensors.

Traditional pulse oximeters, for example, are fairly complex with regard to the required usage of multiple parts having multiple liners, folding operations, etc., during manufacture of the sensor. Specifically, traditional assembly requires that a person manually align multiple layers together, press the layers together (attempting to correctly maintain alignment, avoid bubbles and avoid missing portions). Such sensors can be costly to assemble and may suffer from reliability/repeatability of the build. Less reliable performance may result, for example when layers are not laminated together properly, causing the layers to delaminate (open up) or when layers are not precisely aligned together, for example if the holes for optics to pass light through are not centered well enough on the optics or other materials are out of place, causing pressure points on the patient.

What is needed in the art is a construction of a sensor that eases manufacture and/or remanufacture of the sensor, while increasing reliability and repeatability of such manufacture or remanufacture.

SUMMARY

The techniques of this disclosure generally relate to medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting source, for example a light-emitting diode (LED), communicatively coupled to the communication interface and a detector, communicatively coupled to the communication interface, capable of detecting light. In exemplary embodiments, a bandage is constructed as a single piece such that plural layers of the bandage are configured together to allow for a leaflet opening of the bandage to insert a pulse oximetry circuit therein. In exemplary embodiments, at least one removable internal liner or tab is included as part of the bandage to facilitate opening of the bandage via the leaflet.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, communicatively coupled to the communication interface, capable of detecting light. The patient monitoring sensor further includes a bandage is constructed as a single piece such that plural layers of the bandage are configured together to allow for a leaflet opening of the bandage to insert a pulse oximetry circuit therein. In exemplary embodiments, at least one removable internal liner or tab is included as part of the bandage to facilitate opening of the bandage via the leaflet.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Traditional pulse oximeters, for example, are fairly complex with regard to the required usage of multiple parts having multiple liners, folding operations, etc., during manufacture of the sensor. Such sensors can be costly to assemble and may suffer from reliability/repeatability of the build.

Accordingly, the present disclosure describes a bandage that is constructed as a single piece such that plural layers of the bandage are configured together to allow for a leaflet opening of the bandage to insert a pulse oximetry circuit therein. In exemplary embodiments, the leaflet is converted by a machine to cut the proper shapes, align the shapes together and laminate all layers together. In further exemplary embodiments, at least one removable internal liner or tab is included as part of the bandage to facilitate opening of the bandage via the leaflet.

Figure 1:
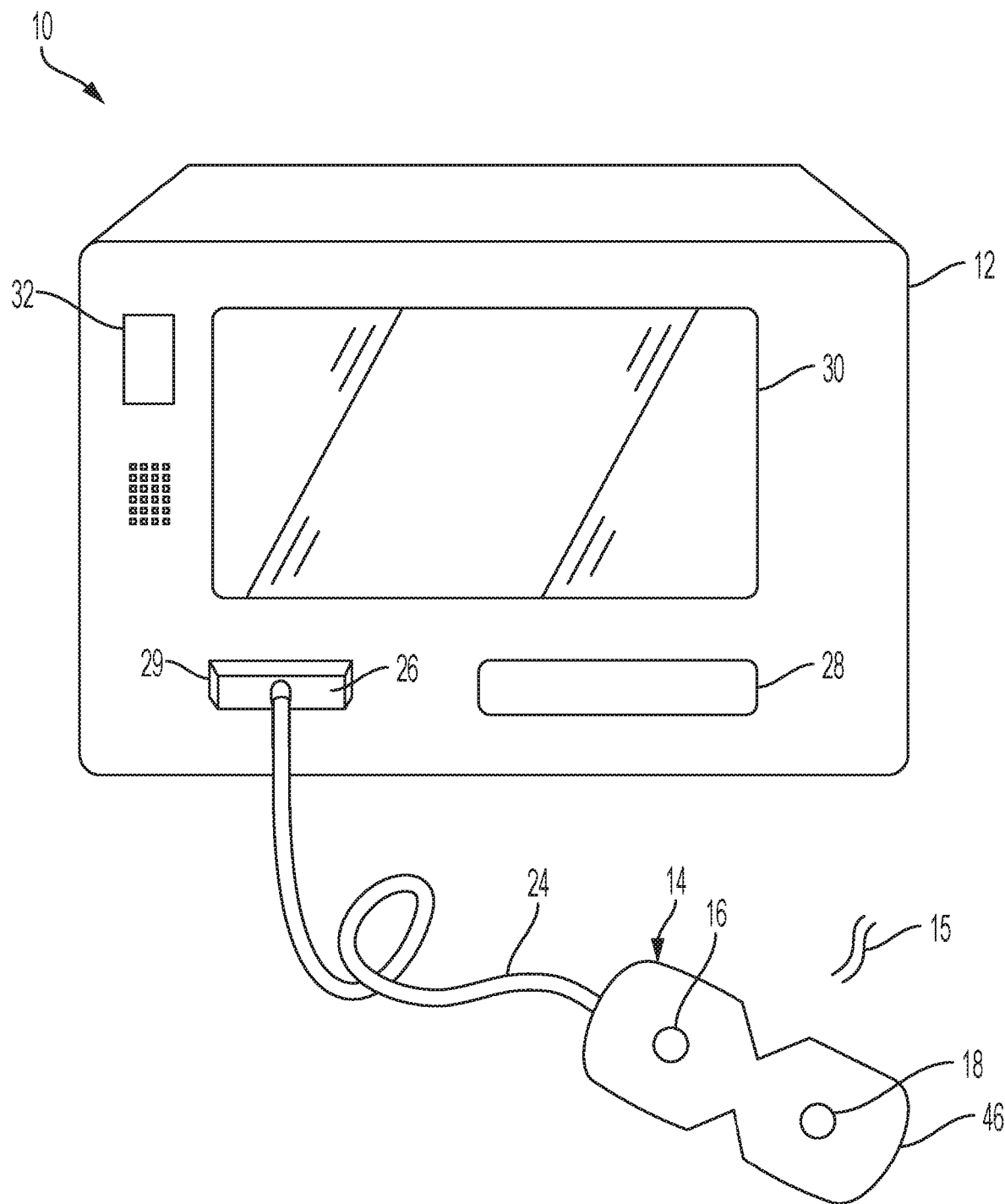
FIG. 1 illustrates a perspective view of an exemplary patient monitoring system including a patient monitor and a patient monitoring sensor, in accordance with an embodiment.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, CO), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal.

The sensor 14 also includes a sensor body 46 to house or carry the components of the sensor 14. The body 46 includes a backing, or liner, provided around the emitter 16 and the detector 18, as well as an adhesive layer (not shown) on the patient side. The sensor 14 may be reusable (such as a durable plastic clip sensor), disposable (such as an adhesive sensor including a bandage/liner at least partially made from hydrophobic materials), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
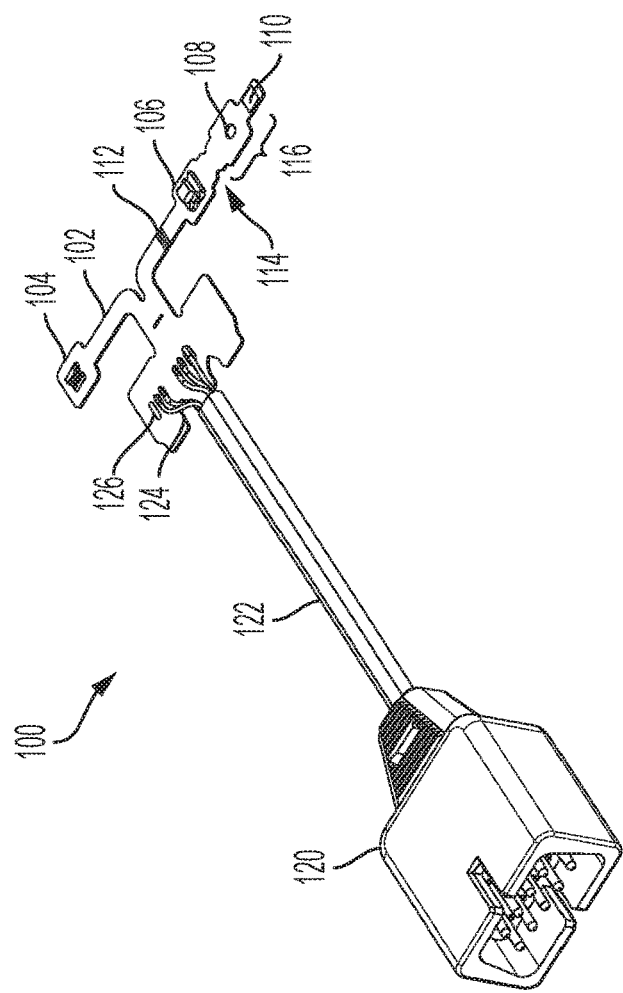
FIG. 2 illustrates a perspective view of an exemplary patient monitoring sensor, in accordance with an embodiment.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes an LED 104 (in this case a surface mount LED) and a detector 106 disposed on the body 102 of the sensor 100.

While any number of exemplary sensor designs are contemplated herein, in the illustrated exemplary embodiment, the body 100 includes a flap portion 116 that includes an aperture 108. The flap portion 116 is configured to be folded at a hinge portion 114 such that the aperture 108 overlaps the detector 106 to allow light to pass through. In one embodiment, the flap portion 116 includes an adhesive 110 that is used to secure the flap portion 116 to the body 102 after the flap portion 116 is folded at the hinge portion 114. The exemplary flap portion 116 increases the surface area to reduce the contact pressure from the detector on the skin.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

In exemplary embodiments, the aperture 108 is configured to provide electrical shielding to the detector 106. In exemplary embodiments, aperture 108 also limits the amount of light that is received by the detector 106 to prevent saturation of the detector. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to provide electrical shielding for the detector 106 and/or control the amount of light that is received by the detector 106. In exemplary embodiments, the body 102 includes a visual indicator 112 that is used to assure proper alignment of the flap portion 116 when folded at the hinge portion 114. Further, the shape of the material of the flap portion 116 around the aperture 108 can vary, while at the same time increasing the surface area around the detector to reduce the contact pressure from the detector on the skin.

Figure 3:
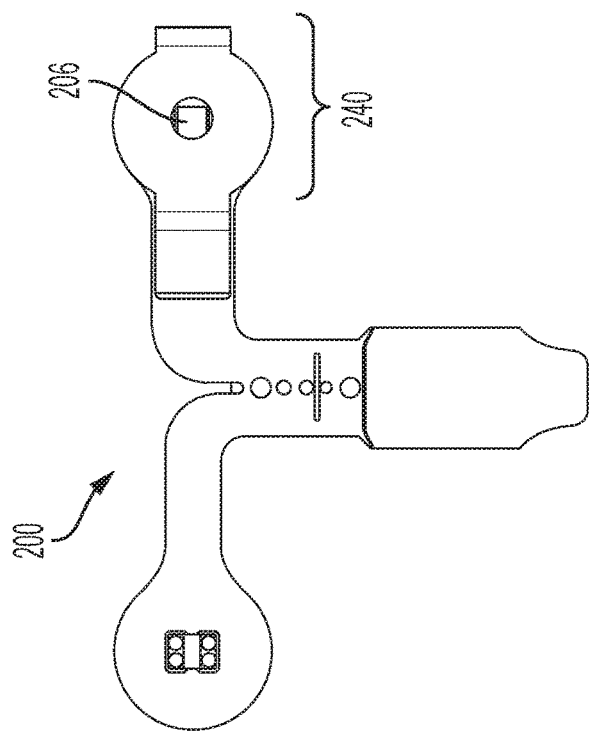
FIG. 3 illustrates a schematic view of an exemplary patient monitoring sensor, in accordance with an embodiment.

Referring now to FIG. 3, a patient monitoring sensor 200 in accordance with an embodiment is shown. In exemplary embodiments, a faraday cage 240 is formed around the detector 206 by folding the flap portion 116 over a portion of the body 102 of the sensor 200.

As we have noted, regardless of sensor configuration particulars of the above-described exemplary embodiments, a bandage is constructed as a single piece such that plural layers of the bandage are configured together to allow for a leaflet opening of the bandage to insert a pulse oximetry circuit therein. In exemplary embodiments, at least one removable internal liner or tab is included as part of the bandage to facilitate opening of the bandage via the leaflet.

Figure 4:
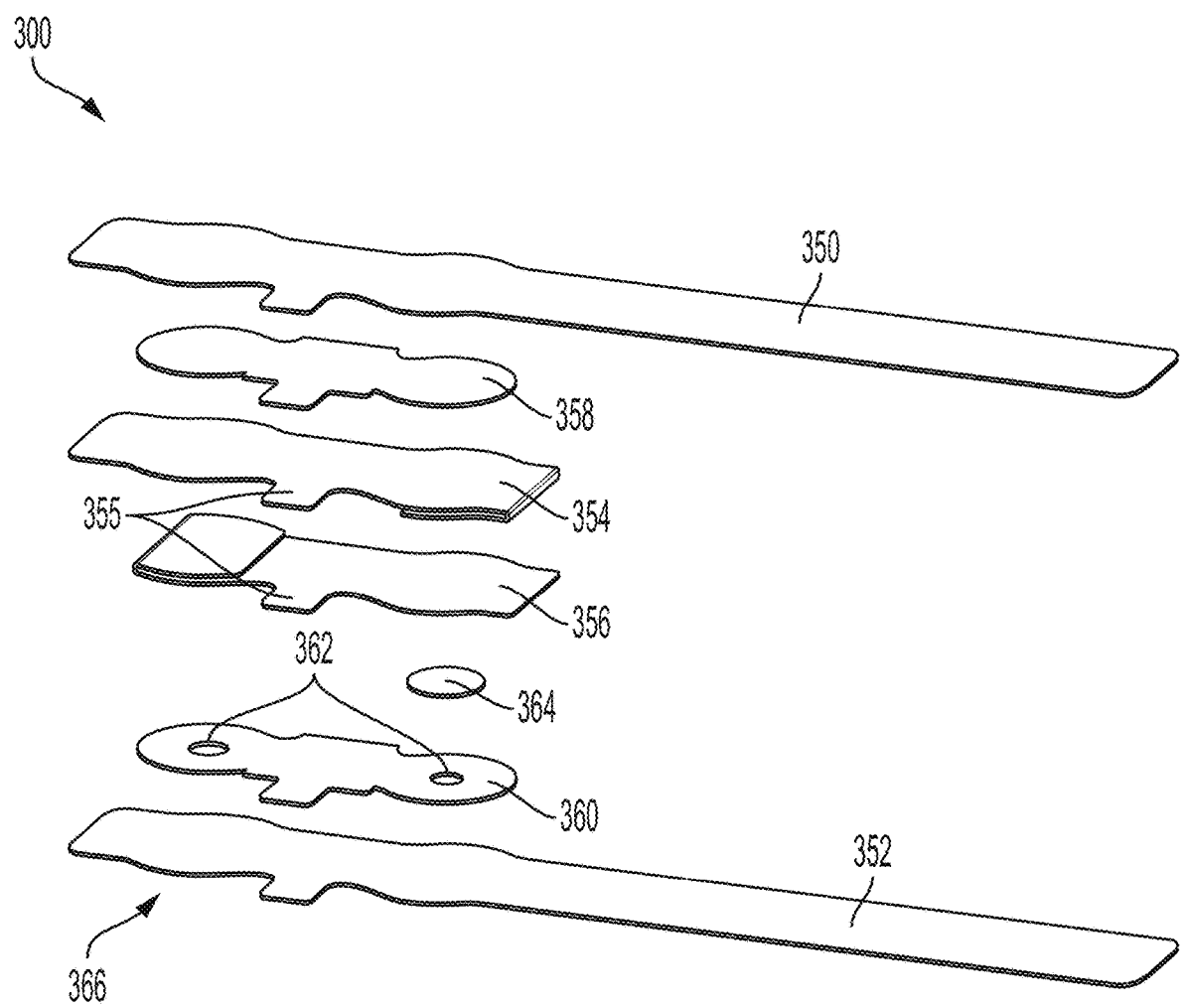
FIG. 4 illustrates a layered schematic view of an exemplary patient monitoring sensor bandage, in accordance with an embodiment.

FIG. 4 illustrates an expanded perspective view generally at 300 of an exemplary layered body/bandage configuration for a pulse oximeter sensor. The configuration includes: an upper bandage 350; an exemplary bottom tape/patient adhesive 352; exemplary top internal liner 354 and bottom internal liner 356, which in exemplary embodiments are discarded during sensor assembly, allowing the bandage to open like a leaflet to insert the flex circuit of FIGS. 2 and 3 into the bandage; a top light blocking layer 358, for example a metallized tape; a bottom light blocking layer 360, for example a metallized tape with holes 362 configured to allow light to shine through; and a disc 364, comprising for example a polyethylene material, configured to reduce pressure from the LED on the patient. In exemplary embodiments, bottom tape 352 comprises an adhesive layer with a release liner 366 on the patient facing side of tape 352.

Figure 5:
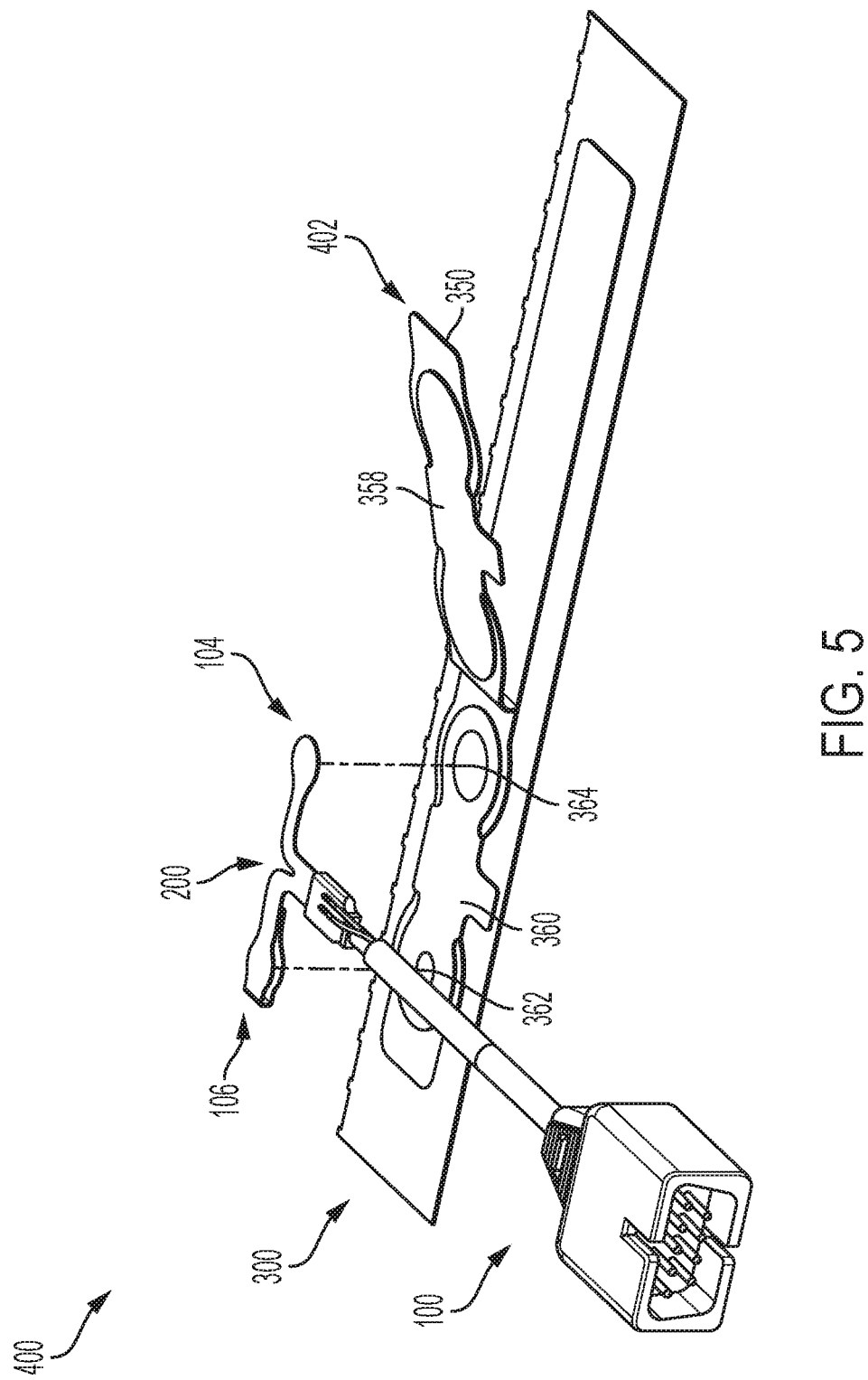
FIG. 5 illustrates a perspective view of an exemplary sensor assembly.

FIG. 5 illustrates a perspective view of exemplary assembly of the flex circuit 200 of FIGS. 2 and 3 into the bandage 300, with internal liners 354, 356 removed to allow positioning of the flex circuit 200 into the bandage, between the light blocking layers 358, 360. As is shown, detector 106 is positioned over hole 362. LED 104 is positioned over disc 364 (which is positioned over another hole 362 (not shown in FIG. 5)). Rapid assembly is facilitated by removable liners 354, 356, as well as the upper bandage 350 and light blocking layer 358 acting as a foldable leaflet 402, the exemplary bandage construction provided as a sub-assembly configured to provide high-volume, fast and repeatable production of sensor assemblies.

Exemplary materials for backing or other material includes plastics, such as polypropylene (PP), polyester (PES), polyethylene (PE), urethanes, silicone, or the like. Additionally, various layers of the device may be constructed of one or more hydrophobic materials. Bandage, backing and additional possible layers may comprise a variety of thicknesses.

In exemplary embodiments, disc 364 is a thin disc (e.g, 0.1 millimeter (mm)polyethylene, which is semi-transparent and is operative to maintain the light transmission from the LED through the PET) inserted in or integral to bandage between the LED and the patient-side of the sensor, e.g., to reduce contact pressure on the skin. Other thicknesses of materials are also contemplated, for example 0.08 mm-0.12 mm; 0.1 mm-0.15 mm, etc. In exemplary embodiments, a PET disc 364 is converted with an acrylic adhesive on one side and die cut into an 8 millimeter (mm) disc (though ranges of sizes are contemplated, e.g., 5-12 mm, 6-10 mm, 7-9 mm, etc.) that is adhered to the bottom tape of the sensor.

In exemplary embodiments, the bottom tape (352 in FIG. 4) has an adhesive facing toward the disc 364, which adheres the disc in place.

In further exemplary embodiments, the LED (104 in FIG. 2) is soldered to the flex circuit (200 in FIG. 3), which is placed on top of the adhesive side of the disc 364 (see FIG. 5). The adhesive of the disc 364 secures the disc in place relative to the LED 104.

Regardless, according to example embodiments described herein, the leaflet 402 configuration provides a bandage as a single piece such that plural layers of the bandage are configured together to allow for the leaflet opening of the bandage to insert a pulse oximetry circuit therein. In exemplary embodiments, at least one removable internal liner or tab is included as part of the bandage to facilitate opening of the bandage via the leaflet.

Figure 6:
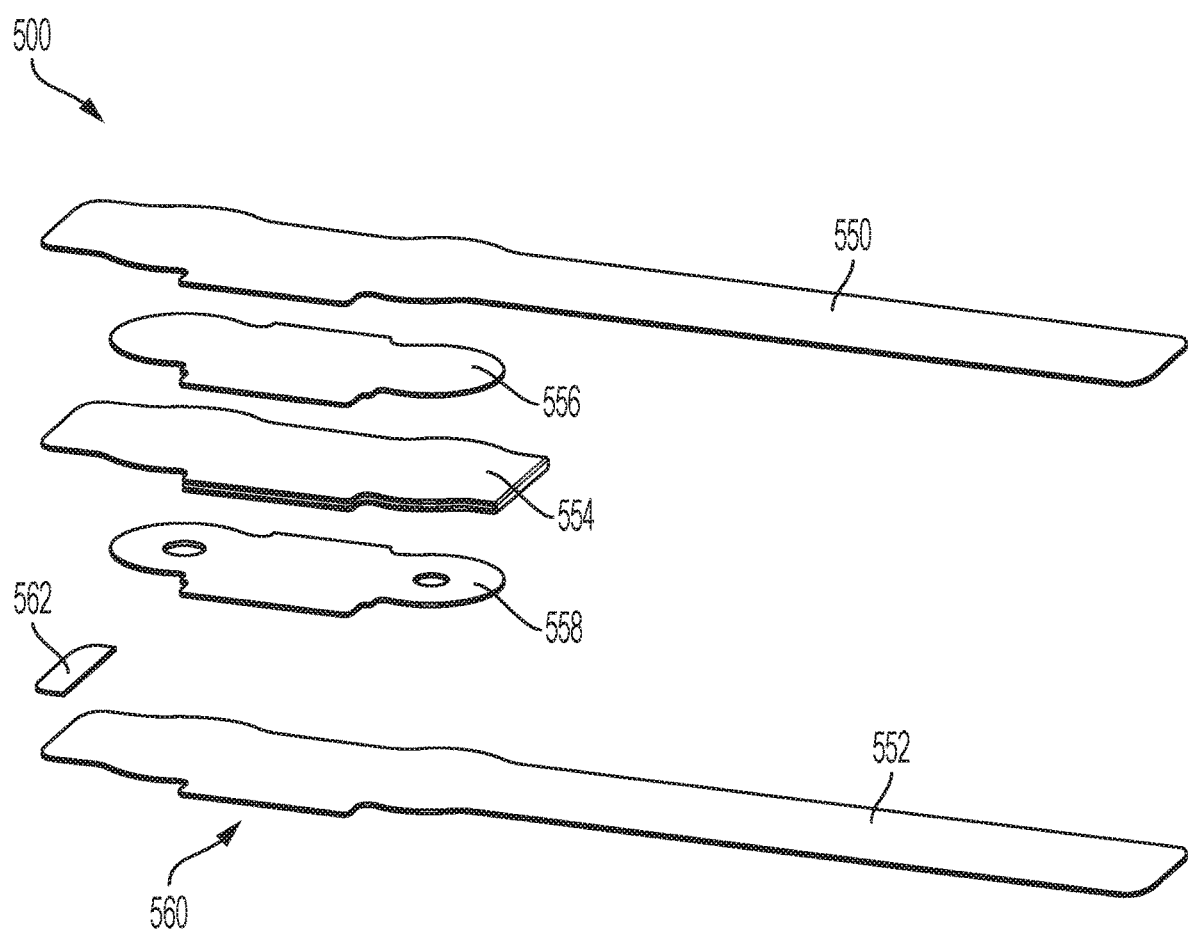
FIG. 6 illustrates a blown-up, perspective view of another exemplary bandage.

FIG. 6 illustrates a, blown-up, perspective view of another exemplary bandage generally at 500. The exemplary bandage 500 includes an upper bandage 550 and an upper metalized tape 556 (providing shielding for sensor components, such as light sources and detectors), inserted into the bandage 500 when the tape 556 and upper bandage 550 are folded backwards as a leaflet. As used herein, the term "leaflet" includes any folding back of the upper bandage 550 such that sensor components may be installed within the bandage, followed by subsequent replacement of the upper bandage over the sensor components. In exemplary embodiments, the leaflet also contains a shielding or reinforcing component, such as the metalized tape 556, that folds back with the upper bandage 550.

In further exemplary embodiments, folding back of the upper bandage 550 is facilitated by at least one removable internal liner 554 (note the two removable liners 354 and 356 in the exemplary embodiment of FIG. 4). In exemplary embodiments, removal of the liner also exposes adhesive used to secure sensor components in the interior of the bandage (between upper and lower bandage components). Tabs 355 on upper and lower liners 354, 356 provide two protruding surfaces that touch each other but that are not adhered to one another. Thus, a user can start an opening in the bandage using those tabs (in conjunction with similar contours above and below those removable liners) to peel the bandage open (in this case, starting on the left side where the tabs 355 are).

Further exemplary embodiments may use other or additional tabs or liners to facilitate folding back of the leaflet, for example the tab 562 in FIG. 6 provided on the lower bandage/tape 552. Such tab 562 can be configured to remove from or remain in a dead space within the single piece bandage. In one exemplary embodiment, a dead zone tab 562 can be a thin, polyethylene film, or the like, without adhesive on either side to facilitate opening of the leaflet.

Referring again the exemplary embodiment illustrated in FIG. 6, a lower metalized tape 558 is also positioned on the lower bandage/tape 552. In exemplary embodiments, the lower bandage/tape comprises a material having a patient-side adhesive 560.

Figure 7:
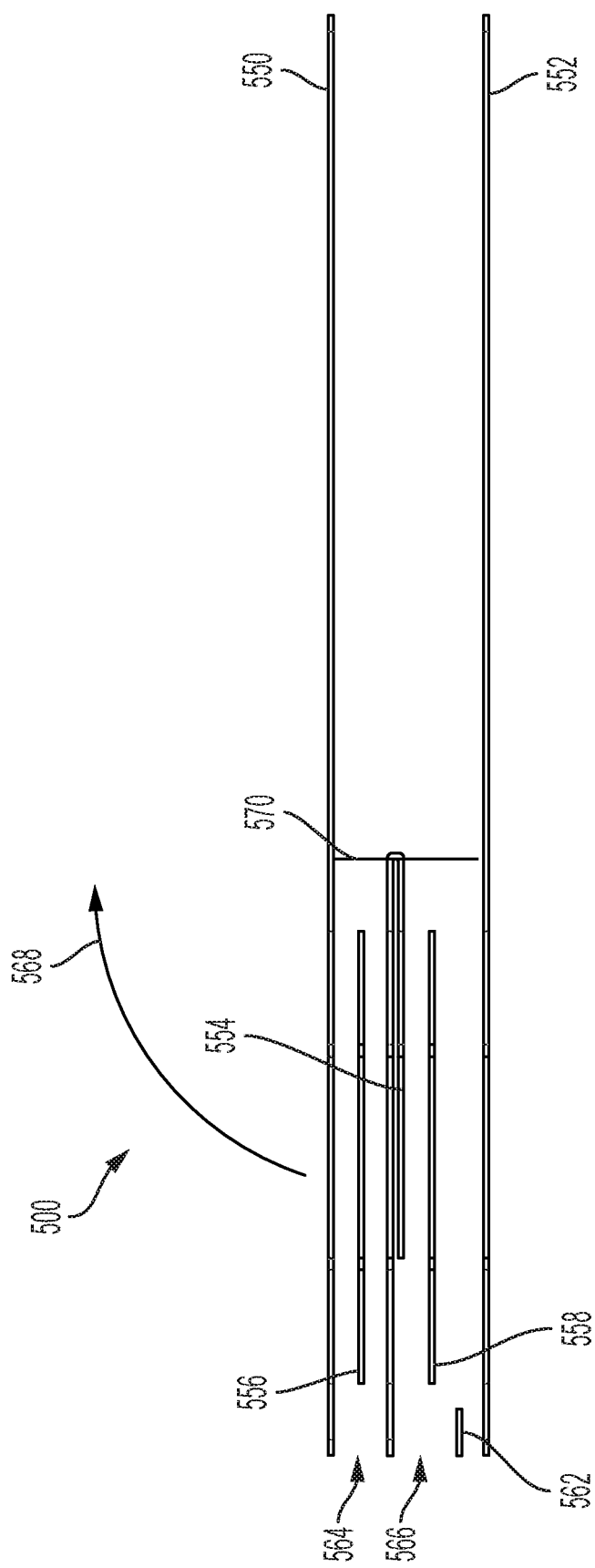
FIG. 7 illustrates an exploded, side schematic view of the exemplary bandage of FIG. 6.

FIG. 7 illustrates an exploded, side schematic view of the exemplary bandage 500 of FIG. 6. Upper and lower bandage portions are generally indicated by the indicated lines 564, 566, respectively. Leaflet portion 568 folds up and back from the lower bandage portion 566, in the direction of arrow 568 by virtue of liner 554, which opens up during the maneuver. An upper surface of liner 554 is adhered to bandage portion 566; and a lower portion is adhered to bandage portion 564. In exemplary embodiments, folding of the leaflet can be also facilitated by visual or fold lines 570 during manufacture or remanufacture. An optional tab 562, e.g., in a dead- or keep out-zone tab can further assist in opening the bandage by covering a portion of the adhesive to liner interface in a specific location (e.g., at one end of the lower bandage) to make it easier for an assembler to open the leaflet.

As we have noted, exemplary embodiments provide a single-piece bandage for a sensor, wherein an upper part of the bandage folds away from a lower bandage part to permit installation of sensor components therein. In further exemplary embodiments, the leaflet folds away along with an upper shielding or reinforcing member. In exemplary embodiments, the upper bandage portion folds away as a leaflet facilitated by at least one removable liner or tab. In exemplary embodiments, a liner 554 comprises a folded material configured to make it easy for the liner to be grabbed and removed during assembly. After removal of, e.g., the internal liner and placement of the electronics, the leaflet can be re-closed, completing the sensor assembly.

Thus, in exemplary embodiments, a one-piece bandage is provided with plural or all layers pre-assembled for manufacture or re-manufacture of the sensor. Exemplary embodiments also facilitate ease of manufacture or re-manufacture and produce reliable and repeatable alignment and contact of the layers, for example by eliminating need to manually align and laminate layers together.

One or more specific embodiments of the present techniques will be described below. In an effort to provide a concise description of these embodiments, not all features of an actual implementation are described in the specification. It should be appreciated that in the development of any such actual implementation, numerous implementation-specific decisions must be made, which may vary from one implementation to another.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A patient monitoring sensor, comprising
   a communication interface, through which the patient monitoring sensor is configured to communicate with a monitor;
   a light-emitting diode (LED) communicatively coupled to the communication interface;
   a detector, communicatively coupled to the communication interface, capable of detecting light; and
   a single piece bandage, comprising:
      an upper bandage portion;
      a lower bandage portion;
      an adhesive configured to secure at least one of the LED or the detector between the upper bandage portion and the lower bandage portion, and
      at least one releasable liner or releasable tab provided between the upper and lower portions to facilitate folding back of the upper bandage portion relative to the lower bandage portion or of the lower bandage portion relative to the upper bandage portion, wherein the upper bandage portion or the lower bandage portion is configured to fold back down over at least one of the LED or the detector when the LED or the detector is inserted between the lower bandage portion and the upper bandage portion, and wherein the at least one releasable liner or releasable tab covers the adhesive.

2. The patient monitoring sensor of claim 1, wherein the releasable liner exposes the adhesive configured to secure the LED or detector at an installation position.

3. The patient monitoring sensor of claim 2, wherein at least one of the upper or lower bandage portions further include a shielding or reinforcing member at the installation position.

4. The patient monitoring sensor of claim 3, wherein the lower bandage portion further comprises at least one at least partially transparent thin material at an LED or detector position.

5. The patient monitoring sensor of claim 3, wherein the lower bandage portion further comprises at least one at ring, the at least one ring defining an aperture therethrough at an LED or detector position.

6. The patient monitoring sensor of claim 1, comprising the at least one releasable liner, wherein the at least one releasable liner comprises upper and lower releasable liners for upper and lower bandage portions at an installation position.

7. The patient monitoring sensor of claim 6, wherein the upper and lower releasable liners are configured to be removed from the single piece bandage to expose the adhesive to secure the LED and/or detector at the installation position.

8. The patient monitoring sensor of claim 1, comprising the at least one releasable liner, wherein the at least one releasable liner comprises a folded material to facilitate separation of upper and lower bandage portions.

9. The patient monitoring sensor of claim 1, wherein at least one of the upper or lower bandage portions further include a fold line.

10. The patient monitoring sensor of claim 1, further comprising a leaflet including a foldable upper bandage portion, the leaflet configured to open for installation of the LED and detector and to close to complete manufacture or re-manufacture of the sensor.

11. A single piece bandage for a patient monitoring system, comprising:
an upper bandage portion;
a lower bandage portion;
an adhesive configured to secure sensor components between the upper bandage portion and the lower bandage portion; and
at least one releasable liner or releasable tab provided between the upper and lower portions to facilitate folding back of the upper bandage portion relative to the lower bandage portion or of the lower bandage portion relative to the upper bandage portion, wherein the upper bandage portion or the lower bandage portion is configured to fold back down over the sensor components inserted between the lower bandage portion and the upper bandage portion, and wherein the at least one releasable liner or releasable tab covers the adhesive.

12. The single piece bandage of claim 11, comprising the at least one releasable liner, wherein the at least one releasable liner exposes the adhesive configured to secure a pulse oximetry LED or detector at an installation position, the sensor components comprising the pulse oximetry LED or the detector.

13. The single piece bandage of claim 12, wherein at least one of the upper or lower bandage portions further include a shielding or reinforcing member at the installation position.

14. The single piece bandage of claim 13, wherein the lower bandage portion further comprises at least one at least partially transparent thin material at an LED or detector position.

15. The single piece bandage of claim 13, wherein the lower bandage portion further comprises at least one at ring, the at least one ring defining an aperture therethrough at an LED or detector position.

16. The single piece bandage of claim 11, comprising the at least one releasable liner, wherein the at least one releasable liner comprises upper and lower releasable liners for upper and lower bandage portions, the liners defining an openable area between the upper and lower bandage portions.

17. The single piece bandage of claim 16, wherein the upper and lower releasable liners expose the adhesive to secure a pulse oximetry LED or detector between the upper and lower bandage portions, the sensor components comprising the pulse oximetry LED or the detector.

18. The single piece bandage of claim 11, wherein the releasable liner comprises a folded material to facilitate separation of upper and lower bandage portions.

19. The single piece bandage of claim 11, wherein at least one of the upper or lower bandage portions further include a fold line.

20. The single piece bandage of claim 11, further comprising a leaflet pulse oximetry LED and detector, wherein the sensor components comprise the leaflet pulse oximetry LED and detector.

* * * * *